(12) United States Patent
Auguet et al.

(10) Patent No.: US 9,080,220 B2
(45) Date of Patent: Jul. 14, 2015

(54) SIMULTANEOUS, SEPARATE OR SEQUENTIAL THERAPEUTIC USE OF AT LEAST ONE BOTULINUM NEUROTOXIN AND OF AT LEAST ONE OPIATE DERIVATIVE

(75) Inventors: Michel Auguet, Palaiseau (FR); Christine Favre, Saint Maurice Montcouronne (FR); Pierre-Etienne Chabrier De Lassauniere, Paris (FR)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 0 days.

(21) Appl. No.: 12/305,191

(22) PCT Filed: Jun. 11, 2007

(86) PCT No.: PCT/FR2007/000956
§ 371 (c)(1),
(2), (4) Date: Dec. 16, 2008

(87) PCT Pub. No.: WO2007/144493
PCT Pub. Date: Dec. 21, 2007

(65) Prior Publication Data
US 2009/0232851 A1    Sep. 17, 2009

(30) Foreign Application Priority Data
Jun. 16, 2006    (FR) ..................... 06 05368

(51) Int. Cl.
| *A61K 38/48* | (2006.01) |
| *A61K 39/08* | (2006.01) |
| *A61K 9/00* | (2006.01) |
| *A61K 31/485* | (2006.01) |
| *A61K 45/06* | (2006.01) |

(52) U.S. Cl.
CPC ....... *C12Y 304/24069* (2013.01); *A61K 31/485* (2013.01); *A61K 38/4893* (2013.01); *A61K 45/06* (2013.01)

(58) Field of Classification Search
CPC ........... A61K 39/3955; A61K 39/4893; A61K 9/019; A61K 38/4893; A61K 2300/00; A61K 2039/02; A61K 2039/54; A61K 31/485; A61K 45/06
See application file for complete search history.

(56) References Cited

U.S. PATENT DOCUMENTS

| 4,457,916 | A | 7/1984 | Hayashi et al. |
| 6,136,551 | A | 10/2000 | Aoki et al. |
| 6,368,605 | B1 | 4/2002 | Donovan |
| 7,704,524 | B2 * | 4/2010 | Donovan ...................... 424/449 |
| 8,273,359 | B2 | 9/2012 | Favre et al. |
| 8,784,841 | B2 | 7/2014 | Favre et al. |
| 2002/0064536 | A1 * | 5/2002 | Hunt ........................... 424/247.1 |
| 2002/0192239 | A1 | 12/2002 | Borodic et al. |
| 2003/0138437 | A1 | 7/2003 | Hunt |
| 2004/0247623 | A1 | 12/2004 | Cady |
| 2005/0147625 | A1 | 7/2005 | First |
| 2005/0152905 | A1 | 7/2005 | Omoigui |
| 2006/0178354 | A1 * | 8/2006 | Lucas .......................... 514/178 |
| 2006/0240043 | A1 | 10/2006 | Meyerson et al. |
| 2006/0269575 | A1 | 11/2006 | Hunt |
| 2008/0232851 | A1 | 9/2008 | Park et al. |
| 2009/0028908 | A1 | 1/2009 | Donovan |
| 2009/0214466 | A1 | 8/2009 | Levin |
| 2009/0232849 | A1 | 9/2009 | Gallez et al. |
| 2009/0232851 | A1 | 9/2009 | Auguet et al. |
| 2010/0029566 | A1 | 2/2010 | Favre et al. |
| 2010/0068231 | A1 | 3/2010 | Favre et al. |
| 2011/0038893 | A1 | 2/2011 | Favre et al. |

FOREIGN PATENT DOCUMENTS

| AU | 2007259122 | 11/2012 |
| CA | 2 586 181 | 5/2006 |
| EP | 1 604 681 | 4/2005 |
| EP | 1 604 681 | 12/2005 |
| EP | 2 037 956 | 2/2014 |
| GB | 2 416 692 | 2/2006 |
| GB | 2 419 526 | 3/2006 |
| KR | 2003018827 | 3/2003 |
| WO | WO 95/17904 | 7/1995 |
| WO | WO 01/26736 | 4/2001 |
| WO | WO 01/47512 | 7/2001 |
| WO | WO 01/58472 | 8/2001 |
| WO | WO 01/76576 | 10/2001 |
| WO | WO 01/78760 | 10/2001 |
| WO | WO 2004/06954 | 1/2004 |
| WO | WO 2004/075832 | 9/2004 |
| WO | WO 2005/082339 | 9/2005 |
| WO | WO 2006/005910 | 1/2006 |
| WO | WO 2006/005912 | 1/2006 |
| WO | WO 2006/042249 | 4/2006 |
| WO | WO 2006/049248 | 5/2006 |
| WO | WO 2007/144493 | 12/2007 |

OTHER PUBLICATIONS

Kern, U., et al. "Long-Term Treatment of Phantom and Stump Pain with Type A Botulinum Toxin for 1 Year, First Clinical Observations", Nervenarzt, vol. 75, No. 4, (Apr. 2004).
Gordon, D., "Pharmacologic Management of Neuropathic Pain", Pain Management Nursing, W.B. Saunders, vol. 5, pp. 19-33, (Dec. 2004).
International Search Report (PCT/ISA/210) for International Application No. PCT/FR2007/000956, mailed on Feb. 22, 2008.
Luvisetto, et al. (2007) *Neuroscience* 145: 1-4.
Meyer (2008) *SA Fam Pract* 50(3): 40-49.

(Continued)

*Primary Examiner* — Nita M Minnifield
(74) *Attorney, Agent, or Firm* — Hunton & Williams LLP

(57) ABSTRACT

The present invention relates to a composition comprising: at least one botulinum neurotoxin, and at least one opiate derivative or its salt. The invention also relates to a product comprising at least one botulinum neurotoxin and at least one opiate derivative or its salt, as a combination product for simultaneous, separate or sequential therapeutic use in the treatment or prevention of pain and of neuromuscular disorders.

12 Claims, 2 Drawing Sheets

(56) References Cited

OTHER PUBLICATIONS

NINDS Peripheral Neuropathy Information Page (2011).
Park & Moon (2008) "Antinociceptive effects of botulinum toxin A for the treatment of neuropathic pain." *Reviews in Analgesia* 10(1): 1-9 [Abstract only].
Sudaraj, et al. (2004) *Pain Practice* 4(3): 229-234.
Barwood, et al. (2000) *Developmental Medicine & Child Neurology* 42: 116-121.
Kern, et al. (2004) *J Rehabil Med* 36: 238-239.
Argoff (2002) *The Clinical Journal of Pain* 18: S177-S181.
Calabrese & Resztak (1998) *Expert Opinion on Investigational Drugs* 7(12): 2043-2060.
Gonzalez-Duarte, et al. (2006) *The PRN Notebook* 11(2): 24-29.
Klein, et al. (2004) *Dematol. Surg.* 30: 452-455.
Bueschen (1990) *Clinical Methods: The History, Physical, and Laboratory Examinations* [3$^{rd}$ Ed.] Chapter 182 "Flank Pain".
Tarantino (2002) *Techniques in Regional Anesthesia and Pain Management* 6(1): 33-38.
Ansiaux, 218 et al. (2007) *Expert Opinion on Investigational Drugs* 16(2): 209-218.
Aoki (2005) *NeuroToxicology* 26(5): 785-793.
Argoff, et al. (2002) *The Journal of Clinical Pain* 18: S177-S181.
Attal, et al. (2008) *Neurology* 70(11): A167.
Auguet, et al. (2008) *Toxicon* 51(Suppl. 1): 9.
Bach-Rojecky, et al. (2005) *Journal of Neural Transmission* 112(2): 215-219.
Bach-Rojecky, et al. (2005) *Basic Science—Croatian Medical Journal* 46(2): 201-208.
Blersch, et al. (2002) *Journal of the Neurological Sciences* 205(1): 59-63.
Cata, et al. (2008) *Brain Research* 1229: 100-110.
Cui et al. *Pain* (2004) 107: 125-133.
Dieleman, et al. (2002) *Archives of Internal Medicine* 162(13): 1492-1501.
Farve-Guilmard, et al. (2009) *European Journal of Pharmacology* 617:48-53.
Favre-Guilmard, et al. (2008) *Toxicon* 51(Supp. 1): 10.
Frich, et al. (2000) *Journal of Pain and Symptom Management* 19(5): 339-347.
Guokai, et al. (2003) *Chinese Journal of Anesthesiology* 23(2): 157-159.
Jabbari, et al. (2003) *Pain Medicine* 4(2): 206-210.
Jacobson, et al. (2008) *Applied and Environmental Microbiology* 74(9): 2778-2786.
Joseph, et al. (2004) *Pain* 107: 147-158.
Keswani, et al. (2002) *AIDS* 16: 2105-2117.
Klein, et al. (2004) *Dermatologic Surgery* 30(3): 452-455.
Ledeboer, A. et al. (2007) *Brain Behavior and Immunity* 21: 686-698.
Liu, et al. (2006) *Pain Medicine* 7(1): 89-91.
Lo Nigro, et al. (2002) *Medical and Pediatric Oncology* 38(2): 150.
Luciano, et al. (2003) *Current Opinion in Neurology* 16: 403-409.
Luvisetto, et al. (2006) *Brain Research* 1082(1): 124-31.
Luvisetto, S., et al. (2007) *NeuroScience* 145: 1-4.
Noguera, et al. (2004) *AIDS* 18(2): 352-353.
Park Hue Jung, et al. (2008) "Antinociceptive Effects of Botulinum Toxin A for the Treatment of Neuropathic Pain." *Reviews in Analgesia* vol. 10, [Abstract only].
Park, et al. (2006) *Canadian Journal of Anesthesia* 53(5): 470-477.
Polomano, et al. (2001) *Pain* 94: 293-304.
Ranoux, et al. (2008) *Annals of Neurology* 64(3): 274-283.
Voller, et al. (2003) *Neurology* 61(7): 940-944.
Yuan, et al. (2009) *Neurology* 72(17): 1473-1478.
Webb, et al. (2006) *Drug Metab Rev.* 38(1-2): 89-116.
The Merck Index: An Encyclopedia of Chemicals and Drugs, 9th Ed., Merck & Co. (1976) p. 814.
International Search Report for International Application No. PCT/IB2009/005750, mailed Jul. 10, 2009.
International Search Report for International Application No. PCT/FR2007/002091, mailed Jul. 29, 2008.
International Search Report for International Application No. PCT/FR2007/001773, mailed Apr. 28, 2008.
Dougherty et al., (2004) Pain 109:132-142.
Gordon, et al. "Pharmacologic management of neuropathic pain." *Pain Management Nursing* (2004) 5: 19-33 [Abstract].
Hill "Phantom Limb Pain: A Review of the Literature on Attributes and Potential Mechanisms" *Journal of Pain and Symptom Management* (1999) 17(2): 125-142.
Kern, et al. "Long-term treatment of phantom and stump pain with type A botulinum toxin for 1 year. First clinical observations" *NERVENARZT* (2004) 75(4): 336-340 [Abstract].
Kidd & Urban "Mechanisms of Inflammatory Pain." *British Journal of Anaesthesia* (2001) 87(1): 3-11.
Khoromi, et al. "Morphine, Nortriptyline and their Combination vs. Placebo in Patients with Chronic Lumbar Root Pain" *Pain* (2007) 130(1-2): 66-75.
Radhakrishnan, et al. *Current Protocols in Pharmacology* (2004) 5.35.1-5.35.28.
Zane, et al. (2007) "Morphine Dosing in Acute Pain: How Much Is Enough?" *NEJM Journal Watch* (2 pages).
Zhang, et al. "Antiangiogenic Treatment with Three Thrombospondin-1 Type 1 Repeats versus Gemcitabine in an Orthotopic Human Pancreatic Cancer Model" *Clin Cancer Res* (2005) 11: 5622-5630.
AFSSAPS, Rapport Public d'Evaluation, Botox 50 Unites Allegan, poudre pour solution injectable, Botox 100 Unites Allergan, poudre pour solution injectable, Botox 200 Unities Allgergan, poudre pour solution injectable (4 pages) a report published by National Security Agency of Medicines and Health Products France (2011).

\* cited by examiner

SIMULTANEOUS, SEPARATE OR SEQUENTIAL THERAPEUTIC USE OF AT LEAST ONE BOTULINUM NEUROTOXIN AND OF AT LEAST ONE OPIATE DERIVATIVE

CROSS-REFERENCE TO RELATED APPLICATIONS

This application is the U.S. National Stage of International Application No. PCT/FR2007/000956 filed on Jun. 11, 2007, which claims the benefit of Application No. FR 0605368 filed in France on Jun. 16, 2006, the disclosures of each of which are herein incorporated by reference in their entirety.

FIELD OF INVENTION

A subject of the present invention is a composition comprising:
   at least one botulinum neurotoxin, and
   at least one opiate derivative or its salt.

A subject of the invention is also a product comprising at least one botulinum neurotoxin and at least one opiate derivative or its salt as a combination product for a therapeutic use which is simultaneous, separate or sequential in the treatment or prevention of pain as well as neuromuscular disorders.

BACKGROUND

Today pain still remains a pathology which is difficult to relieve or to cure.

Use of the compounds currently available which make it possible to reduce pain in a satisfactory manner is often associated with undesirable side effects (for example sedation, habituation, hyperalgesia, risk of ulcers).

It has therefore become necessary to find a means of reducing these risks of side effects. This would make it possible to improve the treatment of pain.

Also the problem that the invention intends to solve is to find a novel treatment for pain.

SUMMARY OF INVENTION

Unexpectedly, the inventors have demonstrated that the combination of botulinum neurotoxin and of morphine or of a morphine analogue or derivative, has a powerful synergistic effect in the treatment of pain to the point of being able to considerably reduce the doses of botulinum toxin and morphine administered to the patient whilst retaining an equivalent analgesic effect. In fact, these two active ingredients administered at subactive doses (i.e. at doses which do not by themselves produce any therapeutic effect), produce, when they are combined, a highly significant therapeutic effect.

To this end the present invention proposes a composition comprising:
   at least one botulinum neurotoxin, and
   at least one opiate derivative or its salt.

The invention also proposes a product comprising at least one botulinum neurotoxin and at least one opiate derivative or its salt as a combination product for a therapeutic use which is simultaneous, separate or sequential in the treatment or prevention of pain and neuromuscular disorders.

The invention offers many advantages, in particular that of reducing the doses of morphine administered. In fact the compositions and products according to the invention can be used at much lower doses compared with the doses of currently commercially available morphine which are usually administered. In other words, in order to obtain the same analgesic effect, a smaller quantity of morphine and botulinum toxin is injected. For the same therapeutic indications, a reduction comprised between 10 to 70%, preferably between 25 to 50%, in the administration doses could be observed (comparison between units of toxins and quantity of morphine (mg/kg) injected in order to obtain the same biological effect).

Another advantage of the compositions or products according to the invention is that they cause few side effects, and in particular far fewer side effects than the botulinum toxin or morphine compositions or products known at present. In particular the possibility of using low doses of compositions or products according to the invention advantageously makes it possible to reduce the side effects. Among the side effects of the botulinum toxin which are avoided, there can be mentioned those linked to the immunogenicity of the protein itself, as well as dysphasia, ptosis or general muscle weakness, this list not being exhaustive. Similarly, among the main side effects of morphine which are avoided, there can be mentioned constipation, nausea, vomiting, confusion, drowsiness, habituation and hyperalgesia.

Finally, the invention has the advantage of being able to be implemented in all industries, in particular the pharmaceutical, veterinary and cosmetic industries.

Other advantages and characteristics of the invention will become clearly apparent on reading the following description and examples which are given purely by way of illustration and are non-limitative.

Firstly, a subject of the present invention is a composition comprising:
   at least one botulinum neurotoxin, and
   at least one opiate derivative or its salt.

DETAILED DESCRIPTION

By the expression botulinum neurotoxin is meant a botulinum toxin which is either a free protein (i.e. free of any protein complexing it), or a protein complex, said protein complex being able to comprise for example hemagglutinin (HA) protein combined with botulinum toxin, or a protein fragment.

By the expression botulinum toxin is meant a molecule possessing the biological activity of the botulinum toxin, which can be for example either a protein, or a polypeptide, or a peptide, or a fusion protein, or a truncated protein, or a chimeric protein, or a mutated protein or a recombinant protein.

By the expression biological activity of the toxin is meant within the meaning of the present invention either a muscle paralysis or inhibition of exocytosis, in particular exocytosis of acetylcholine or of another neurotransmitter.

By protein, polypeptide or peptide is meant within the meaning of the present invention, a polymer of natural or non-natural, levorotary or non-levorotary, dextrorotary or non-dextrorotary amino acids.

By chimeric protein is meant within the meaning of the present invention a protein obtained after combination of different types of molecules, for example after combination of lipids, glycolipids, peptides, polypeptides, proteins, glycoproteins, carbohydrates, polysaccharides, nucleic acids, polyethylene glycol etc.

The botulinum toxin, in particular the botulinum toxin type A1 (DYSPORT® (botulinum toxin type A) marketed by Ipsen or BOTOX® marketed by Allergan), has been used in humans since the 1980s for the treatment of various diseases/disorders. Among the diseases/disorders which can be treated with botulinum toxin, there can be mentioned inter alia muscle disorders (for example the blepharospasm, spasticity in adults or children or also torticollis), migraine, pain of muscular origin, neuropathic pain, diabetes, hyperhidrosis (or excessive perspiration), hypersalivation or even wrinkles.

Uses of the botulinum toxins known at present relate to its standard, intramuscular administration as described in the treatments mentioned. Injection into the muscles causes their temporary paralysis, i.e. blocks muscle contractions over a certain period of time.

The pure or virtually pure botulinum neurotoxin can be obtained from a protein complex comprising botulinum toxin for example according to the method described in *Current topics in Microbiology and Immunology* (1995), 195, p. 151-154. A pure or virtually pure botulinum neurotoxin can be obtained for example, by purification of a fermentation medium or culture medium containing a strain of *Clostridium Botulinum*, and enriched for example with meat or protein-rich food.

The composition according to the invention comprises:
at least one botulinum neurotoxin, and
at least one opiate derivative or its salt.

Preferably, the composition according to the invention comprises at least one botulinum neurotoxin of type A, A1, A2, B, C, C1, D, E, F or G.

The botulinum neurotoxin type A1 corresponds in fact to the standard botulinum toxin which is commonly called botulinum toxin type A, without distinction of subtype. The botulinum neurotoxin type A1 is marketed under the name of DYSPORT® or RELOXIN® or BOTOX®.

According to the invention, the botulinum neurotoxin type A1 can correspond either to a complex of botulinum toxin A1 and hemagglutinin, or to the botulinum toxin type A1 free of all complexing proteins.

The botulinum toxin type A2 was first isolated from cases of children suffering from botulism around 1990 (Sakaguchi et al., *Int. J. Food Microbiol.* (1990), 11, 231-242). This toxin is immunologically and biochemically different from the botulinum toxin type A1.

The botulinum toxin type A2 can be isolated from the following strains: Kyoto-F, Chiba-H, Y-8036, 7103-H, 7105-H, KZ1828, NCTC2012 or NCTC9837 (Cordoba et al., *System. Appl. Microbiol.* (1995), 18, 13-22; Franciosa et al., abstract presented at 40$^{th}$ Interagency Botulism Research Coordinating Committee (IBRCC) Meeting, November 2003).

Preferably, the composition according to the invention comprises the botulinum toxin type A1.

According to a variant the composition according to the invention comprises the botulinum toxin type A2 isolated from the strain *Clostridium botulinum* referenced and accessible under number NCTC9837, at the National Collection of Type Cultures—Central Public Health Laboratory—London—UK. The strain NCTC9837 is sometimes called the Mauritius 1955 strain.

The botulinum toxin type A2 differs from the toxin A1 by inter alia, its amino acid sequence, its molecular weight, its immunological and genetic characteristics (Kubota et al., *Biochem. Biophys. Res. Commun.* (1996), 224 (3), 843-848).

The composition according to the invention comprises at least one opiate derivative or its salt.

By the expression "opiate derivative or its salt" is meant within the meaning of the present invention, the substances commonly called "opiates", and in particular morphine analogues or derivatives. In fact morphine, currently well-known for its anti-pain effects was itself isolated right at the start of the 19$^{th}$ century by a German pharmacist, Friedrich Sertürner, from the opium of which it is the main constituent.

According to a variant, the composition according to the invention comprises at least one opiate derivative or its salt chosen from the morphine analogues or derivatives, fentanyl, alfentanil, codeine, dihydrocodeine, hydrocodone, oxycodone, hydromorphone, pethidine, remifentanyl, sufentanil, dextropropoxyphene, tramadol, buprenorphine, nalbuphine, morphine sulphate, hydromorphone hydrochloride or coated morphine sulphate.

By salt is meant a pharmaceutically acceptable salt and in particular inorganic acid addition salts such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. Salts formed from bases such as sodium or potassium hydroxide also fall within the scope of the present invention, when they can be used. For other examples of pharmaceutically acceptable salts, reference can be made to "Salt selection for basic drugs", *Int. J. Pharm.* (1986), 33, 201-217.

The present composition according to the invention can moreover comprise at least one polysaccharide or a mixture of several polysaccharides.

By polysaccharide is meant within the meaning of the present invention, a polymer comprising at least 2 monomers, the monomers being saccharides. This definition includes the disaccharides.

Within the framework of the invention, the polysaccharides can be ionic and/or non ionic.

Preferably, the composition comprises at least one polysaccharide comprising mostly glucose units. The term "mostly" signifying that glucose accounts for the majority of the monomer units.

As examples of suitable polysaccharides according to the invention, there can be mentioned starch, starch derivatives, hydroxyethyl starch in particular 2-hydroxy-ethyl starch.

The suitable polysaccharides according to the present invention can be substituted, in particular can be substituted by alkyl, alkoxy radicals or also by alkyl radicals themselves substituted by alcohol groups.

According to a variant of the invention, the quantity of polysaccharide comprised in the composition according to the invention is at least 1 µg of polysaccharide per 1 unit of botulinum toxin. According to the choice of polysaccharide, it is possible to use at least 0.5 µg of polysaccharide per 1 unit of botulinum toxin.

The present composition according to the invention can moreover comprise at least one surfactant or a mixture of several surfactants.

By surfactant is meant within the meaning of the invention an emulsifying agent or a solubilizing agent.

Within the framework of the invention the surfactants utilized can be chosen from the cationic, anionic or non-ionic surfactants.

Preferably, the composition according to the invention comprises at least one surfactant chosen from the non-ionic surfactants of the polysorbates group.

From the polysorbates group, there can be mentioned polysorbate 20, polysorbate 21, polysorbate 40, polysorbate 60, polysorbate 61, polysorbate 65, polysorbate 80, polysorbate 81, polysorbate 85, polysorbate 120, polysorbate 80 acetate.

The preferred surfactant according to a variant of the composition according to the invention is polysorbate 80.

A subject of the present invention is also the composition described above for its use as a medicament.

The composition according to the invention can be in solid form, for example powders, freeze-dried products, granules, tablets or liposomes. The composition according to the invention in solid form can be stored for example at temperatures below 4° C., or below 0° C. without its biological activity being altered.

The composition according to the invention can be presented in the form of an aqueous dispersion of particles of botulinum neurotoxin in a gelled lattice.

The composition according to the invention can also be presented in liquid form, for example, solutions, emulsions or suspensions.

The administration of the composition according to the invention is carried out preferably by injection such as for example by intramuscular or sub-cutaneous injection.

In the case of injections, the composition according to the invention can be combined with an agent facilitating the injection also called an injection vehicle or injection vector.

According to an embodiment of the compositions according to the invention, the ratio of the botulinum neurotoxin unit fractions to the quantity of opiate derivative or its salt [BT units/mg of opiate derivative] can be comprised between 0.1/1000 and 1000/0.1, preferably between 80/200 and 200/80, still more preferably between 10/333 and 333/10, advantageously between 0.3/10 and 10/0.3.

A subject of the present invention is also the use of a composition according to the invention, described above, for obtaining a medicament intended to treat or prevent pain, in particular pain associated with cancer, pain associated with chronic diseases other than cancer, neuropathic pain, pain associated with radiculopathy, diabetic neuropathy or associated with AIDS or resulting from AIDS or antineoplastic agents, inflammatory pain, adiposis dolorosa, pain associated with burns, migraine, pre- and post-operative pain, chronic inflammatory pain, sciatica, post-herpes neuralgia, fibromyalgia, algoneurodystrophy or complex regional pain syndrome and central pain resulting from cerebral vascular accidents, thalamic lesions or multiple sclerosis, or physical pain: trauma, or pain associated with intoxication.

A subject of the present invention is also the use of a composition according to the invention, described above, for obtaining a medicament intended to treat or prevent cosmetic defects, muscular disorders, neuromuscular disorders, neurological disorders, orthopedic disorders, ophthalmological disorders, psychological disorders, articular pathology, endocrine disorders or urological disorders.

A subject of the present invention is also the use of a composition according to the invention, described above, for obtaining a medicament intended to treat or prevent torticollis, spasmodic torticollis, local spasticity disorders of the upper and/or lower limbs, pain, muscular pain, pain due to muscle spasms, myofacial pain, post-operative pain, muscle spasms, hemifacial spasm, blepharospam, strabismus, facial asymmetry, muscular dystonia, cerebral palsy, headache, migraine, fibromyalgia, myalgia, depressive states, hyperhidrosis, bromhidrosis, coxarthrosis, hip arthrosis, epicondylitis of the elbow, arthritis, rheumatoid arthritis, dyskinesia, achalasia, Oddi's sphincter dysfunctions, pancreatitis, gout, anal fissures, constipation, anismus, spasms of the pyloric valve, spastic bladder, bladder spasms, urinary incontinence, urine retention, prostate hyperplasia, endometriosis, psoriasis, rhinitis, allergic rhinitis, obesity, hyperlacrimation, bone fractures, tendon lacerations or rotator muscle cap pathology of the shoulder.

A subject of the present invention is also the use of a composition according to the invention, described above, for obtaining a cosmetic product.

A subject of the present invention is also the use of a composition according to the invention, described above, for obtaining a medicament intended to treat or prevent facial frown lines, facial wrinkles, wrinkles of the skin, wrinkles of the contour of the eye, wrinkles of the glabella, glabellar frown lines, baldness, acne, excessive perspiration or hair loss.

Preferably, the composition according to the invention is used in order to obtain a medicament intended to treat or prevent pain.

By "pain" within the meaning of the present invention is meant "any unpleasant emotional and sensory experience associated with existing or potential tissue damage or described by the patient in such terms".

Among pains that can be treated by a composition or a product according to the invention, there can be mentioned in particular:

pain associated with cancer (particularly preferred to the extent that the botulinum neurotoxin is also an antineoplastic agent);

pain associated with chronic diseases other than cancer such as pain associated with viral or retroviral diseases (for example pains associated with Acquired Immunodeficiency Syndrome (AIDS) or pains linked with herpes zoster) or pain associated with diabetic neuropathies;

neuropathic pain such as trigeminal neuralgia, glosso-pharyngeal neuralgia, pain associated with radiculopathies and pain associated with neuropathies secondary to metastatic infiltrations;

adiposis dolorosa;

pain associated with burns;

pain due to a migraine;

pre- and post-operative pain;

chronic pain, fibromyalgia, algoneurodystrophy or complex regional pain syndrome central pain resulting from cerebral vascular accidents, thalamic lesions or multiple sclerosis.

A subject of the present invention is also, as a medicament, the composition according to the invention described above.

A subject of the present invention is also a pharmaceutical composition comprising the composition according to the invention described above.

The dose of the composition according to the present invention, to be provided for the treatment of the abovementioned diseases or disorders, varies depending on the administration method, the age and the body weight of the subject to be treated as well as the state of the latter, and will be finally decided by the attending doctor or vet. Such a quantity determined by the attending doctor or vet is here called the "therapeutically effective quantity".

The therapeutically effective quantity which should be injected also varies according to the number of muscles to be treated, as well as according to the mass of these muscles.

Preferably, the injected doses of botulinum neurotoxins, comprised in the composition according to the invention, are comprised between 0.1 and 1000 units of botulinum toxin, more preferably 1 to 500 units of botulinum toxin, still more preferably 5 to 100 units of botulinum toxin, whatever the type of botulinum toxin or whatever its provenance.

Preferably, the injected doses of morphine are comprised between 0.001 and 0.3 mg per kg/day.

A subject of the invention is also a product comprising at least one botulinum neurotoxin and at least one opiate derivative or its salt as a combination product for therapeutic use which is simultaneous, separate or sequential in the treatment or prevention of pain, cosmetic defects, muscular disorders, neuromuscular disorders, neurological disorders, orthopedic disorders, ophthalmological disorders, psychological disorders, articular pathology, endocrine disorders or urological disorders.

By simultaneous therapeutic use, within the meaning of the present invention is meant in the present Application a administration of at least 2 active ingredients by the same route and at the same time or at substantially the same time.

By separate use, within the meaning of the present invention is meant in particular an administration of at least 2 active ingredients at the same time or at substantially the same time by different routes.

By sequential therapeutic use is meant administration of at least 2 active ingredients at different times, the administration route being identical or different. More particularly by an administration method is meant according to which the whole administration of one of the active ingredients is carried out before administration of the other or others commences. It is thus possible to administer one of the active ingredients over several months before administering the other active ingredient or ingredients. There is no simultaneous treatment in this case. An alternate administration of each active ingredient over several weeks can also be envisaged.

Preferably, the product according to the invention is used in the treatment or prevention of pain, in particular pain associated with cancer, pain associated with chronic diseases other than cancer, neuropathic pain, pain associated with radiculopathies, with diabetic neuropathies or associated with AIDS or resulting from AIDS or antineoplastic agents, inflammatory pain, adiposis dolorosa, pain associated with burns, migraine, pre- and post-operative pain, chronic inflammatory pain, sciatica, post-herpes neuralgia, fibromyalgia, algoneurodystrophy or complex regional pain syndrome and central pain resulting from cerebral vascular accidents, thalamic lesions or multiple sclerosis, or physical pain: trauma, amputations, or pain associated with intoxication.

Preferably, the product according to the invention is used in the treatment or prevention of disorders chosen from torticollis, spasmodic torticollis, local spasticity disorders of the upper and/or lower limbs, pain, muscular pain, pain due to muscle spasms, myofacial pain, post-operative pain, muscle spasms, hemifacial spasm, blepharospam, strabismus, facial asymmetry, muscular dystonia, cerebral palsy, headache, migraine, fibromyalgia, myalgia, depressive states, hyperhidrosis, bromhidrosis, coxarthrosis, hip arthrosis, epicondylitis of the elbow, arthritis, rheumatoid arthritis, dyskinesia, achalasia, Oddi's sphincter dysfunctions, pancreatitis, gout, anal fissures, constipation, anismus, spasms of the pyloric valve, spastic bladder, bladder spasms, urinary incontinence, urine retention, prostate hyperplasia, endometriosis, psoriasis, rhinitis, allergic rhinitis, obesity, hyperlacrimation, bone fractures, tendon lacerations or rotator muscle cap pathology of the shoulder.

Preferably, the product according to the invention is used in the treatment or prevention of the disorders of facial frown lines, facial wrinkles, wrinkles of the skin, wrinkles of the contour of the eye, wrinkles of the glabella, glabellar frown lines, baldness, acne, excessive perspiration or hair loss.

Still more preferably, the product according to the invention is used in the treatment or prevention of pain, as defined above.

Preferably, the botulinum neurotoxin used in the product according to the invention can comprise at least one botulinum neurotoxin of type A, A1, A2, B, C, C1, D, E, F or G.

Preferably, the opiate derivative or its salt used in the product according to the invention is chosen from the morphine analogues or derivatives, fentanyl, alfentanil, codeine, dihydrocodeine, hydrocodone, oxycodone, hydromorphone, pethidine, remifentanyl, sufentanil, dextropropoxyphene, tramadol, buprenorphine, nalbuphine, morphine sulphate, hydromorphone hydrochloride or coated morphine sulphate.

According to a variant of the invention, the product according to the invention comprises at least one botulinum neurotoxin of type A, A1, A2, B, C, C1, D, E, F or G, and at least one opiate derivative or its salt chosen from the morphine analogues or derivatives, fentanyl, alfentanil, codeine, dihydrocodeine, hydrocodone, oxycodone, hydromorphone, pethidine, remifentanyl, sufentanil, dextropropoxyphene, tramadol, buprenorphine, nalbuphine, morphine sulphate, hydromorphone hydrochloride or coated morphine sulphate.

In a general manner, what has been described above concerning the botulinum neurotoxin comprised in the composition according to the invention is valid for the botulinum neurotoxin comprised in the product according to the invention.

What has been written above concerning the opiate derivative or its salt comprised in the composition according to the invention is valid for the opiate derivative or its salt comprised in the product according to the invention.

The product according to the invention, and in particular the botulinum neurotoxin, can moreover comprise at least one polysaccharide or a mixture of several polysaccharides as described above, at least one surfactant or a mixture of several surfactants as described above.

The product according to the invention can be presented inter alia in the form of a solid, liquid or aqueous dispersion, as described above.

The administration route of the product according to the invention can be by injection such as for example by intramuscular or sub-cutaneous injection for the botulinum neurotoxin.

The administration route of the product according to the invention can be by topical, oral or parenteral route, by intramuscular, intravenous, sub-cutaneous injection etc. for the opiate derivative or its salt.

The administration route of the product according to the invention is preferably by intramuscular injection for the botulinum neurotoxin and preferably by oral route for the opiate derivative or its salt.

In the case of injections, the product according to the invention can be combined with an agent facilitating the injection also called an injection vehicle or injection vector.

According to an embodiment of the compositions according to the invention, the ratio of the fractions of botulinum neurotoxin units to the quantity of opiate derivative or its salt [BT units/mg of opiate derivative] can be comprised between 0.1/1000 and 1000/0.1, preferably between 80/200 and 200/80, still more preferably between 10/333 and 333/10, advantageously between 0.3/10 and 10/0.3.

Figure 1:
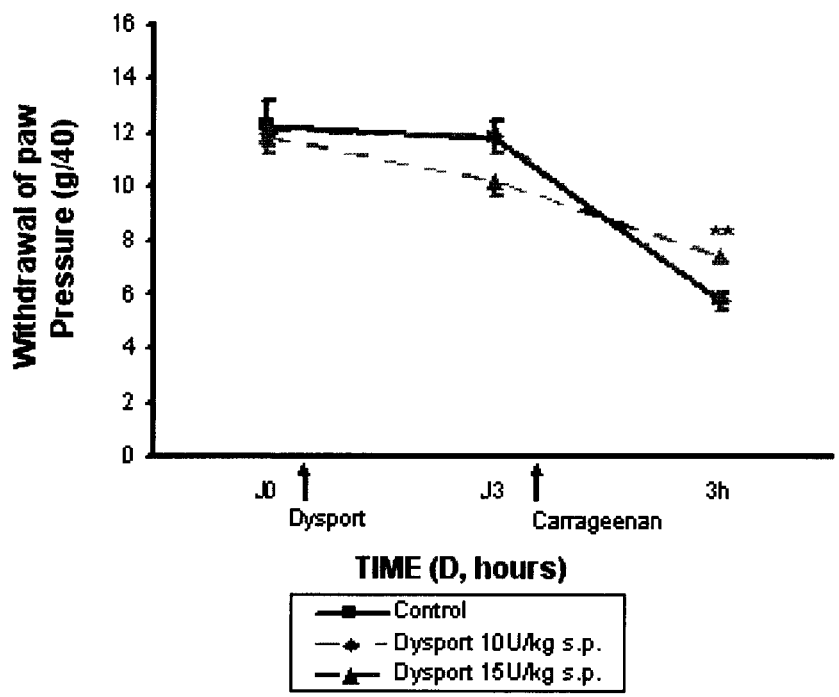
FIG. 1 shows the effect of the botulinum toxin type A following injection by subplantar route in the model of inflammatory hyperalgesia induced by carrageenan.

The following examples illustrate the invention without limiting its scope.

EXAMPLES

The quantification of the botulinum neurotoxins used according to the invention was carried out by measuring a lethal dose $LD_{50}$. By $LD_{50}$ is meant within the meaning of the present invention the lethal dose or also semi-lethal dose of a given substance. It is the dose (or quantity) which leads to the death of 50% of the animals tested in a group. A unit of toxin (U) corresponds to the $LD_{50}$ in mice by intraperitoneal route.

Pharmacological Study of the Products of the Invention

The activity of the compositions of the invention was evaluated in vivo on a model of inflammatory hyperalgesia induced by carrageenan on a rat's paw.

Male Sprague Dawley (Charles River) rats weighing 190 to 210 g on the day of the experiment are kept indoors for 5 to 8 days under animal house conditions and starved on grids for 18 hours before and during the experiment. The groups are made up of at least 8 animals. The botulinum toxin (DYSPORT® (botulinum toxin type A) or its vehicle is administered, 3 days before the carrageenan hyperalgesia experiment, by subplantar route (s.p., 20 μl/paw) into the rat's two rear paws. Morphine (X in FIG. 4) or its vehicle is administered, on the day of the experiment, by intraperitoneal route (i.p., 2 ml/kg), 2 h 30 after the injection of carrageenan. The 2% carrageenan was injected by subplantar route into the rats' right rear paw. The pain threshold (or nociceptive threshold) was evaluated by measuring the withdrawal of the rat's paw in response to a mechanical stimulus the pressure of which increases (initial pressure of 210 $g/mm^2$) applied using an analgesia meter (Randall-Selitto test). The measurements were carried out before the injection of botulinum toxin (initial test on D0) and just before the injection of carrageenan (D3 or t=−2 hours 30 minutes) and 30 minutes (or 3 hours after the carrageenan), 1 hours, 2 hours 30 minutes and 4 hours after the injection of the morphine or its vehicle (carried out at t=0).

In the experiment with the toxin alone, the experimental protocol is identical to that mentioned above without the injection of morphine or its vehicle, the carrageenan hyperalgesia experiment is carried out on D3 and the first measurement of activity at the same time of 3 hours after the carrageenan (i.e. 2 hours 30 minutes+30 minutes).

In the experiment with the morphine alone, the experimental protocol is identical to that mentioned above without the injection of botulinum toxin or its vehicle on D0, the measurements of the analgesic effects are carried out just before the injection of carrageenan (t=−2 hours 30 minutes) and 30 minutes (or 3 hours after the carrageenan), and 2 hours 30 minutes after the injection of the morphine or its vehicle (carried out at t=0).

The effectiveness of the products is evaluated by their ability to significantly reduce hyperalgesia induced by carrageenan. This effectiveness is statistically determined by a Student's test and Satterthwaite's test (two paths).

Figure 4:
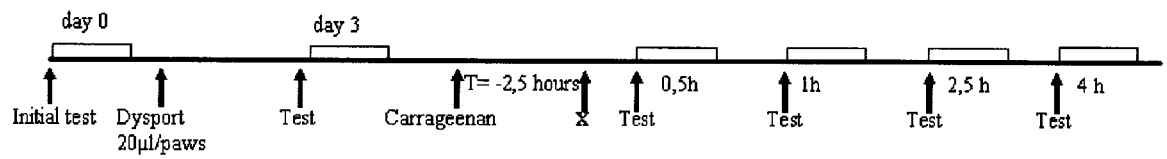
FIG. 4 shows the injection protocol.

The experimental protocol can be found in FIG. 4.

Example 1

Effect of the Botulinum Toxin (DYSPORT® (Botulinum Toxin Type A) on Hyperalgesia Induced by Carrageenan The results obtained using DYSPORT® (botulinum toxin type A) in the model of inflammatory hyperalgesia induced by carrageenan on a rat's paw described above are reported in FIG. 1.

The analgesic effect of the DYSPORT® (botulinum toxin type A) is demonstrated in the hyperalgesia induced by carrageenan test. At a dose of 15 U/kg (s.p.) and on the $3^{rd}$ day, the pain threshold following a mechanical stimulus applied to the rats' paws, is increased by 46% whereas at a dose of 10 U/kg no statistically significant protection against the hyperalgesia induced by carrageenan is observed.

Example 2

Effect of Morphine on Hyperalgesia Induced by Carrageenan

Figure 2:
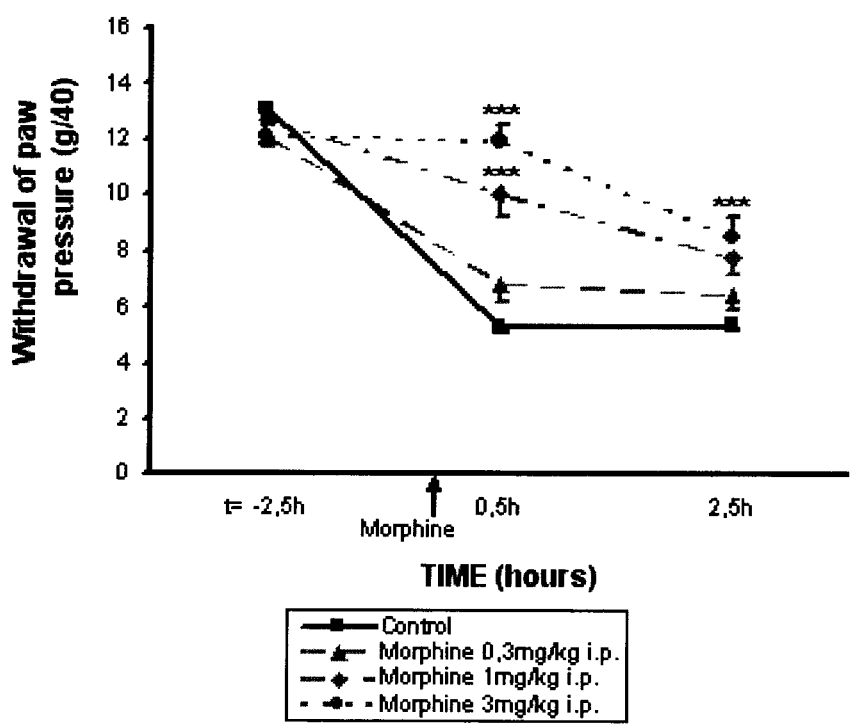
FIG. 2 shows the effect following injection by intra-peritoneal route of morphine in the model of inflammatory hyperalgesia induced by carrageenan.

The results obtained using morphine in the model of inflammatory hyperalgesia induced by carrageenan on a rat's paw described above are reported in FIG. 2.

The analgesic effect of morphine is demonstrated in the hyperalgesia induced by carrageenan test. Starting from a dose of 1 mg/kg (i.p.) the pain threshold following a mechanical stimulus applied to the rats' paws, is increased by 65% and up to 97% for a dose of 3 mg/kg whereas a dose of 0.3 mg/kg does not induce statistically significant protection against hyperalgesia induced by carrageenan.

Example 3

Figure 3:
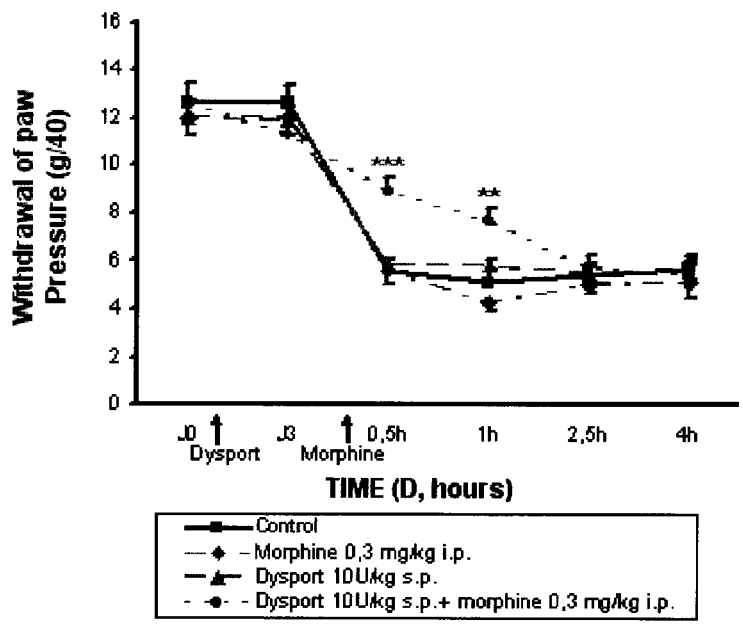
FIG. 3 shows the effect following sequential injections of botulinum toxin type A by subplantar route and of morphine by intra-peritoneal route in the model of inflammatory hyperalgesia induced by carrageenan.

Effect of the Combination of DYSPORT® (Botulinum Toxin Type A) and Morphine on Hyperalgesia Induced by Carrageenan The results obtained using a combination of DYSPORT® (botulinum toxin type A) and morphine in the model of inflammatory hyperalgesia induced by carrageenan on a rat's paw which is described above, are reported in FIG. 3. The administration protocol is indicated in FIG. 4, the term "X" corresponds to the injection of the morphine or its vehicle.

An analgesic effect is observed with the combination of non-active doses of DYSPORT® (botulinum toxin type A) (10 U/kg s.p.) and morphine (0.3 mg/kg i.p.) (in other words, a synergetic effect is observed). By comparing with the results of Examples 1 and 2, it is therefore noted that the administration of DYSPORT® (botulinum toxin type A) and morphine has an synergetic analgesic effect when they are combined. In fact, the use of DYSPORT® (botulinum toxin type A) makes it possible to reduce by at least a factor of 2 the doses of morphine necessary to obtain an equivalent effect. In the same way, the use of morphine makes it possible to reduce by at least a factor greater than 1.5 the doses of DYSPORT® (botulinum toxin type A) necessary to obtain an equivalent effect.

The invention claimed is:

1. A method for treating inflammatory pain in a patient comprising administering a composition comprising at least one dose of botulinum neurotoxin and at least one dose of opiate derivative or salt thereof to a patient in need thereof,
  wherein said botulinum toxin neurotoxin and said opiate derivative or salt thereof and are administered in subactive dosages,
  wherein said dose of botulinum neurotoxin ranges from 0.1 and 10 units/Kg, wherein said dose of botulinum neurotoxin is administered by subcutaneous injection,
  wherein the amount of said dose of opiate derivative or salt thereof ranges from 0.001 to 0.3 mg/Kg, wherein said dose of opiate derivative or salt thereof is administered by intraperitoneal injection, and
  wherein the combined dose of botulinum neurotoxin and the dose of opiate derivative or salt thereof exhibits a synergistic analgesic effect.

2. The method of claim 1, wherein said botulinum neurotoxin is a botulinum neurotoxin of type A, A1, A2, B, C, C1, D, E, F, or G.

3. The method of claim 1, wherein said at least one opiate derivative or salt thereof comprises one or more morphine analogues or derivatives.

4. The method of claim 3, wherein said one or more morphine analogues or derivatives is fentanyl, alfentanil, codeine, dihydrocodeine, hydrocodone, oxycodone, hydromorphone, pethidine, remifentanyl, sufentanil, dextropropoxyphene, tramadol, buprenorphine, nalbuphine, morphine sulphate, hydromorphone hydrochloride, coated morphine sulphate, or a combination thereof.

5. The method of claim 1, wherein said composition further comprises at least one polysaccharide.

6. The method of claim 5, wherein said at least one polysaccharide is 2-hydroxy-ethyl starch.

7. The method of claim 1, wherein said composition comprises at least one surfactant or a mixture of surfactants.

8. The method of claim 7, wherein at least one of the surfactants is a non-ionic surfactant of the polysorbate group.

9. The method of claim 1, wherein the botulinum neurotoxin is a botulinum neurotoxin of type A, A1, A2, B, C, C1, D, E, F, or G; and said at least one opiate derivative or salt thereof comprises one or more morphine analogues or derivatives.

10. The method of claim 9, wherein said one or more morphine analogues or derivatives is fentanyl, alfentanil, codeine, dihydrocodeine, hydrocodone, oxycodone, hydromorphone, pethidine, remifentanyl, sufentanil, dextropropoxyphene, tramadol, buprenorphine, nalbuphine, morphine sulphate, hydromorphone hydrochloride, coated morphine sulphate, or a combination thereof.

11. The method of claim 1, wherein said subactive dosage of the botulinum neurotoxin is an amount insufficient to cause therapeutic effect without the administration of said opiate derivative or salt thereof.

12. The method of claim 1, wherein said subactive dosage of the opiate derivative or salt thereof is an amount insufficient to cause therapeutic effect without administration of said botulinum neurotoxin.

* * * * *